(12) United States Patent
Adachi et al.

(10) Patent No.: US 12,059,299 B2
(45) Date of Patent: Aug. 13, 2024

(54) ULTRASONIC PROBE, ULTRASONIC DIAGNOSTIC SYSTEM, METHOD OF CONTROLLING ULTRASONIC PROBE, AND NON-TRANSITORY COMPUTER-READABLE RECORDING MEDIUM

(71) Applicant: Socionext Inc., Kanagawa (JP)

(72) Inventors: Naoto Adachi, Yokohama (JP); Hiroshi Kishi, Yokohama (JP); Hiroaki Takagi, Yokohama (JP)

(73) Assignee: SOCIONEXT INC., Kanagawa (JP)

( * ) Notice: Subject to any disclaimer, the term of this patent is extended or adjusted under 35 U.S.C. 154(b) by 40 days.

(21) Appl. No.: 17/567,507

(22) Filed: Jan. 3, 2022

(65) Prior Publication Data
US 2022/0117578 A1 Apr. 21, 2022

Related U.S. Application Data

(63) Continuation of application No. PCT/JP2019/026807, filed on Jul. 5, 2019.

(51) Int. Cl.
*A61B 8/00* (2006.01)

(52) U.S. Cl.
CPC .............. *A61B 8/4472* (2013.01); *A61B 8/54* (2013.01); *A61B 8/565* (2013.01)

(58) Field of Classification Search
CPC ......... A61B 8/4472; A61B 8/54; A61B 8/565; A61B 8/4477
See application file for complete search history.

(56) References Cited

U.S. PATENT DOCUMENTS

2002/0181417 A1 12/2002 Malhotra et al.
2012/0179037 A1* 7/2012 Halmann ............... A61B 8/585
600/443

(Continued)

FOREIGN PATENT DOCUMENTS

CN 102579079 A 7/2012
CN 102958135 A 3/2013

(Continued)

OTHER PUBLICATIONS

Chinese Office Action dated Mar. 28, 2023 issued in the corresponding Chinese Patent Application No. 201980098008.7, with English translation.

(Continued)

*Primary Examiner* — Alexei Bykhovski
(74) *Attorney, Agent, or Firm* — Rimon P.C.

(57) ABSTRACT

An ultrasonic probe includes a wireless transmitter-receiver configured to perform communication through a wireless network having a plurality of channels and obtain identification information of apparatuses connected to the wireless network from the apparatuses; a memory configured to store identification information for identifying other ultrasonic probes from among the apparatuses; and a processor configured to count other ultrasonic probes connected with the wireless network on a per channel basis with respect to the plurality of channels based on the identification information obtained by the wireless transmitter-receiver and the identification information stored in the memory, and determine to connect to a channel at which the number of the other ultrasonic probes counted by the processor is smallest.

8 Claims, 12 Drawing Sheets

(56) References Cited

U.S. PATENT DOCUMENTS

2013/0039181 A1    2/2013   Chao
2015/0312833 A1   10/2015   Gresset et al.

FOREIGN PATENT DOCUMENTS

| CN | 110392375 | * | 10/2019 |
|---|---|---|---|
| DE | 102004040279 | * | 3/2005 |
| DE | 102008044423 | * | 2/2009 |
| JP | H08331033 | * | 12/1996 |
| JP | 2010-172409 A | | 8/2010 |
| JP | 2010172409 | * | 8/2010 |
| JP | 2011-000236 A | | 1/2011 |
| JP | 2011-083362 A | | 4/2011 |
| JP | 2011-087840 A | | 5/2011 |
| JP | 2012-143555 A | | 8/2012 |
| JP | 2012119939 | * | 2/2014 |
| JP | 2015204551 | * | 10/2017 |
| TW | 201309055 | * | 11/2014 |
| WO | WO2014046780 | * | 3/2014 |

OTHER PUBLICATIONS

International Search Report and Written Opinion issued in International Patent Application No. PCT/JP2019/026807, dated Oct. 1, 2019; with partial English translation.
Notification of the Second Office Action issued in corresponding Chinese patent application No. 201980098008.7, dated Sep. 13, 2023 w/English MT.
Chinese Office Action dated Jan. 26, 2024 issued in the corresponding Chinese Patent Application No. 201980098008.7, with English machine translation.

* cited by examiner

ULTRASONIC PROBE, ULTRASONIC DIAGNOSTIC SYSTEM, METHOD OF CONTROLLING ULTRASONIC PROBE, AND NON-TRANSITORY COMPUTER-READABLE RECORDING MEDIUM

CROSS-REFERENCE TO RELATED APPLICATION

The present application is a continuation of international application No. PCT/JP2019/026807, filed on Jul. 5, 2019, and designated the U.S., the entire contents of which are incorporated herein by reference.

BACKGROUND OF THE INVENTION

1. Field of the Invention

The present invention relates to an ultrasonic probe, an ultrasonic diagnostic system, a method of controlling an ultrasonic probe, and a non-transitory computer-readable recording medium.

2. Description of the Related Art

An ultrasonic diagnostic system, which has an ultrasonic probe, which outputs an ultrasonic wave to a subject, receives an ultrasonic wave reflected by the subject, and produces an ultrasonic image from the reflected ultrasonic wave, is known. Recently, an ultrasonic probe has become more compact and wireless. For example, a signal obtained from a reflected ultrasonic wave from a living body is processed in the ultrasonic probe to produce ultrasonic image data. The ultrasonic probe wirelessly transmits the generated ultrasonic image data to a terminal apparatus.

In this type of a wireless-communication-type ultrasonic diagnostic system, for example, the terminal apparatus stores probe information identifying the ultrasonic probe to be connected, and the ultrasonic probe stores a device key identifying the terminal apparatus. Then, as a result of the ultrasonic probe responding only to a call from the terminal apparatus corresponding to the device key, the terminal apparatus and the ultrasonic probe are wirelessly connected together correctly even when a plurality of wireless communication type ultrasonic diagnostic systems are used in a common space.

The terminal apparatus stores identification data identifying ultrasonic probes to be connected, and establishes synchronization with an ultrasonic probe when the same identification data as that received from the ultrasonic probe is included in the identification data stored by the terminal apparatus.

PRIOR ART DOCUMENTS

Patent Documents

[Patent Document 1] Japanese Patent Application Publication No. 2011-000236
[Patent Document 2] Japanese Patent Application Publication No. 2011-087840

SUMMARY

In one aspect of a disclosed art, an ultrasonic probe includes a wireless transmitter-receiver configured to perform communication through a wireless network having a plurality of channels and obtain identification information of apparatuses connected to the wireless network from the apparatuses; a memory configured to store identification information for identifying other ultrasonic probes from among the apparatuses; and a processor configured to count other ultrasonic probes connected with the wireless network on a per channel basis with respect to the plurality of channels based on the identification information obtained by the wireless transmitter-receiver and the identification information stored in the memory, and determine to connect to a channel at which the number of the other ultrasonic probes counted by the processor is smallest from among the plurality of channels.

The object and advantages of the invention will be implemented and attained by the elements and combinations particularly pointed out in the appended claims.

It is to be understood that both the foregoing general description and the following detailed description are exemplary and explanatory and are not restrictive of the invention as claimed.

BRIEF DESCRIPTION OF DRAWINGS

Other objects and further features of embodiments will become apparent from the following detailed description when read in conjunction with the accompanying drawings, in which.

DESCRIPTION OF EMBODIMENTS

In the related art, when a plurality of wireless-communication-type ultrasonic diagnostic systems are used in a common space, connecting a terminal apparatus to an ultrasonic probe using a congested channel can slow down wireless communication and, in the worst case, can shut off wireless communication. For example, a decrease in a size and a frame rate of ultrasonic image data to be transmitted wirelessly can compensate for a decrease in a communication speed. However, a quality of an image is deteriorated, and there is a possibility that subsequent imaging diagnosis may be adversely affected.

The disclosed art has been contrived in view of the foregoing point, and it is an object of the disclosed art to perform wireless communication between an ultrasonic probe and a terminal apparatus satisfactorily even when a plurality of ultrasonic diagnostic systems are used in a common space.

Hereinafter, embodiments will be described with reference to the drawings.

First Embodiment

Figure 1:
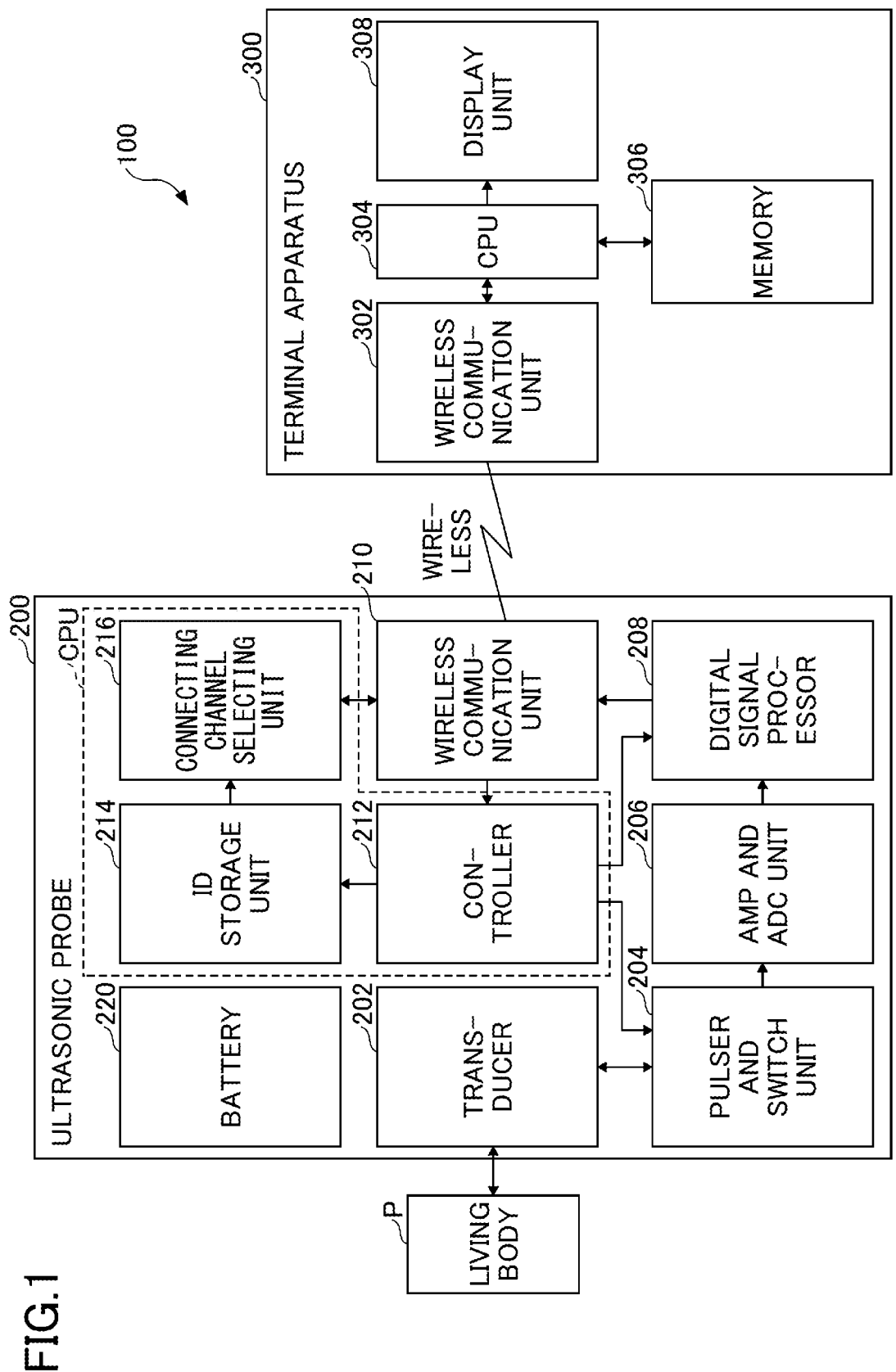
FIG. 1 is a diagram depicting an example of a configuration of an ultrasonic diagnostic system according to a first embodiment.

FIG. 1 depicts an example of a configuration of an ultrasonic diagnostic system 100 of a first embodiment. The ultrasonic diagnostic system 100 depicted in FIG. 1 includes an ultrasonic probe 200 and a terminal apparatus 300. The ultrasonic probe 200 and the terminal apparatus 300 communicate wirelessly with each other. For example, the terminal apparatus 300 may be a general purpose terminal, such as a tablet terminal.

The ultrasonic probe 200 includes a transducer 202, a pulser and switch unit 204, an amplifier (AMP) and analog to digital converter (ADC) unit 206, a digital signal processor 208, and a wireless communication unit 210. The ultrasonic probe 200 further includes a controller 212, an identification information (ID) storage unit 214, a connecting channel selecting unit 216, and a battery 220. For example, as enclosed by a dashed-line rectangle indicated as "CPU" in the ultrasonic probe 200, respective functions of the controller 212, the ID storage unit 214, and the connecting channel selecting unit 216 are implemented by a processor such as a central processing unit (CPU) provided in the ultrasonic probe 200. It is also possible that the respective functions of the controller 212, the ID storage unit 214, and the connecting channel selecting unit 216 may be implemented by hardware logic. The CPU is an example of a processor that executes a program for controlling the ultrasonic probe 200.

The terminal apparatus 300 includes a wireless communication unit 302, a CPU 304, a memory 306, and a display unit 308. The ultrasonic probe 200 outputs ultrasonic waves to a living body P (a subject), receives reflected waves (ultrasonic waves) reflected by the living body P, and generates ultrasonic image data based on the received reflected waves. The ultrasonic probe 200 wirelessly transmits the generated ultrasonic image data to the terminal apparatus 300. The terminal apparatus 300 displays the ultrasonic image data received from the ultrasonic probe 200 as an ultrasonic image on the display unit 308.

The transducer 202 has an oscillator array (not depicted) arranged in an array at a position opposite to a portion of the transducer 202 contacting the living body P (the subject) and outputs ultrasonic waves generated by the oscillator array based on pulse signals generated by the pulser and switch unit 204 to the living body P. The ultrasonic waves entering the living body P are reflected at boundaries with respect to different acoustic impedances. The transducer 202 receives ultrasonic waves (reflected waves) reflected from the living body P and outputs the received ultrasonic waves as signals to the pulser and switch unit 204.

The pulser and switch unit 204 selects the transducer 202 by a switch and transmits the pulse signals from a pulser to the transducer 202 to cause the transducer 202 to output the ultrasonic waves. The pulser and switch unit 204 receives the pulse signals generated by the transducer 202 based on the reflected waves and outputs the received signals to an amplifier of the AMP and ADC unit 206 selected by the switch.

The AMP and ADC unit 206 amplifies the signals representing the reflected waves of the ultrasonic waves received from the pulser and switch unit 204 by the amplifier, converts the signals to digital signals by the ADC, and outputs the digital signals to the digital signal processor 208.

The digital signal processor 208 performs various processes on the digital signals received from the AMP and ADC unit 206 to generate ultrasonic image data and outputs the generated ultrasonic image data to the wireless communication unit 210. For example, the digital signal processor 208 performs a process of aligning timings of the signals representing the reflected waves output from the pulser and switch unit 204, a process of averaging (a phasing and summing process), a gain correction process taking into consideration attenuation of the reflected waves in the living body P, and an envelope process for obtaining brightness information. The digital signal processor 208 transmits the ultrasonic image data to the wireless communication unit 210 using, for example, a serial peripheral interface (SPI).

Figure 2:
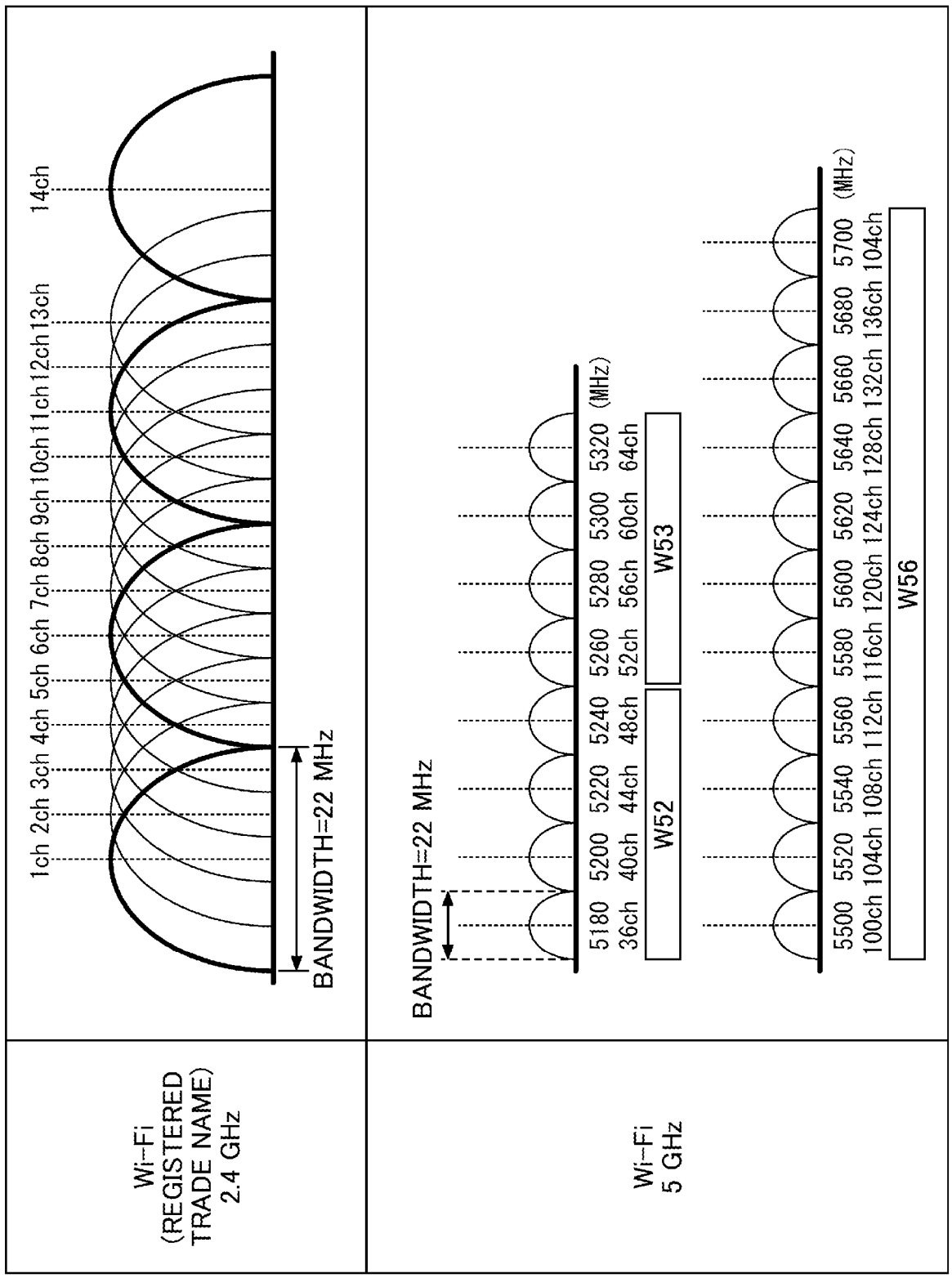
FIG. 2 is a diagram depicting an example of channel assignment in a band of Wi-Fi 2.4 GHz and a band of Wi-Fi 5 GHz.

The wireless communication unit 210 communicates wirelessly with the wireless communication unit 302 of the terminal apparatus 300 external to the ultrasonic probe 200 through a wireless network such as a Wi-Fi (registered tradename, a type of a wireless local area network (LAN)) network. As depicted in FIG. 2, a Wi-Fi network has a plurality of channels. Wireless communication between the wireless communication units 210 and 302 is not limited to communication using a Wi-Fi network, and may be implemented using another wireless standard using a plurality of channels. The wireless communication unit 210 outputs an ultrasonic wave emission instruction or the like received from the terminal apparatus 300 to the controller 212 using, for example, an I-squared-C ($I^2C$) interface. The wireless communication unit 210 transmits ultrasonic image data received from the digital signal processor 208 to the wireless communication unit 302 of the terminal apparatus 300. Ultrasonic image data to be transmitted from the ultrasonic probe 200 to the terminal apparatus 300 is a digital signal (digital data). The wireless communication unit 210 obtains identification information (ID) of apparatuses connected to the Wi-Fi network.

The controller 212 controls the entire ultrasonic probe 200. For example, the controller 212 is implemented by a control program executed by the processor such as the CPU which controls operations of the ultrasonic probe 200. For example, the controller 212 controls the pulser and switch unit 204 to output ultrasonic waves to the transducer 202 in accordance with an instruction for starting a measurement received from the terminal apparatus 300 via the wireless communication unit 210. The controller 212 causes the digital signal processor 208 to generate ultrasonic image data for displaying an image representing reflected waves received from the living body P.

The controller 212 stops operations of the pulser and switch unit 204, the digital signal processor 208, and the like in response to an instruction to stop a measurement received from the terminal apparatus 300 via the wireless communication unit 210. An instruction to start a measurement and an instruction to stop a measurement may be based on an operator's operations of an operation switch provided on a surface of a casing of the ultrasonic probe 200.

The ID storage unit 214 stores identification information (ID) to identify ultrasonic probes of types similar to a type of the ultrasonic probe 200. For example, the ID storage unit 214 may be allocated in an internal memory of the CPU of the ultrasonic probe 200. "Ultrasonic probes of types similar to a type of the ultrasonic probe 200" may be ultrasonic probes of the same type as the type of the ultrasonic probe 200 or different types of ultrasonic probes. For example, if the transducer 202 of the ultrasonic probe 200 is of a linear type, an ultrasonic probe having the transducer of a convex type may be "an ultrasonic probe of a type similar to a type of the ultrasonic probe 200". The ID storage unit 214 is an example of a memory, and ultrasonic probes of types similar to the type of the ultrasonic probe 200 are an example of other ultrasonic probes.

For example, as ID of an ultrasonic probe, a portion of a service set identifier (SSID) that identifies a Wi-Fi access point is used. For example, a SSID of an ultrasonic probe may be set to include a string indicating a type, etc. Hereinafter, ID stored in the ID storage unit 214 is also called unique ID. Unique ID is used to identify ultrasonic probes (other ultrasonic probes) of types similar to the type of the ultrasonic probe 200.

The ID for identifying ultrasonic probes of types similar to the type of the ultrasonic probe 200 is stored in the ID storage unit 214 before the ultrasonic probe 200 begins operation, i.e., before ultrasonic data is obtained from the living body P by the ultrasonic diagnostic system 100. For example, the controller 212 stores ID, received from the terminal apparatus 300 through the wireless communication unit 210, in the ID storage unit 214.

The connecting channel selecting unit 216 determines a connecting channel based on the ID for identifying ultrasonic probes of types similar to the type of the ultrasonic probe 200 stored by the ID storage unit 214 and ID of apparatuses connected to the Wi-Fi network obtained by the wireless communication unit 210. For example, the function of the connecting channel selecting unit 216 is implemented by a control program executed by the CPU of the ultrasonic probe 200. The function of the connecting channel selecting unit 216 is an example of a function of counting other ultrasonic probes of types similar to the type of the ultrasonic probe 200 connected with the Wi-Fi network on a per channel basis, and determining to connect to a channel at which the number of the counted other ultrasonic probes is smallest. An example of operations of the connecting channel selecting unit 216 will be described with reference to FIG. 5.

The battery 220 is chargeable, for example, via a power supply terminal (not depicted) to provide power to each element of the ultrasonic probe 200. The battery 220 may be chargeable in a contactless manner. The ultrasonic probe 200 may operate also using an external power source. In this case, the ultrasonic probe 200 need not include the battery 220.

The wireless communication unit 302 of the terminal apparatus 300 receives ultrasonic image data or the like from the wireless communication unit 210 of the ultrasonic probe 200. The wireless communication unit 302 transmits an ultrasonic wave emission instruction or the like to the wireless communication unit 210 of the ultrasonic probe 200. The CPU 304 controls the entire operations of the terminal apparatus 300, for example, by executing a program. The memory 306 stores ultrasonic image data received by the wireless communication unit 302, various programs executed by the CPU 304, and data used by the various programs.

The display unit 308 displays an ultrasonic image received from the ultrasonic probe 200 or the like. The ultrasonic image displayed on the display unit 308 is a moving image obtained during scanning of the living body P by the ultrasonic probe 200 or a still image obtained when the scanning of the living body P by the ultrasonic probe 200 is stopped. When the terminal apparatus 300 is a general purpose terminal such as a tablet terminal, the display unit 308 may include a touch panel.

FIG. 2 depicts an example of channel allocation in a Wi-Fi 2.4 GHz band and a Wi-Fi 5 GHz band. In the Wi-Fi 2.4 GHz band, 14 channels (1ch-14ch) each having a bandwidth 22 MHz are allocated at 5 MHz intervals, except for a 14ch. A center of a band of each channel is covered by respective bands of the predetermined number of adjacent channels.

A term "band center covering channel" with respect to a certain channel is defined as a channel whose band (having the bandwidth of 22 MHz) covers a band center of the certain channel. For example, with respect to each of 2ch and 3ch of FIG. 2, 1ch is a "band center covering channel"; with respect to each of three channels 1ch, 3ch, and 4ch, the channel 2ch is a "band center covering channel". With respect to each of four channels 1ch, 2ch, 4ch, and 5ch, the channel 3ch is a "band center covering channel". With respect to each of two channels ch11 and ch12, a channel ch13 is a "band center covering channel". A channel ch14 is not a "band center covering channel" with respect to any other channel.

For example, if communication traffic is large and a wide band is used for communication, a band of a channel may overlap an adjacent channel, causing interference between the channels. Because the bands of channels ch1, ch6, ch11, and ch14 depicted in FIG. 2 indicated by thick lines do not overlap each other, interference does not occur with respect to each other. In a third embodiment which will be described later, the channels are classified as groups including: a group of three channels 1ch-3ch, a group of five channels 4ch-8ch, a group of five channels 9ch-13ch, and a group of one channel 14ch, where 1ch, 6ch, 11ch, and 14ch are referred to as center channels of the respective groups.

In the Wi-Fi 5 GHz band, 19 channels each having a bandwidth of 20 MHz are allocated at 20 MHz intervals for a 5.2 GHz band (W52), a 5.3 GHz band (W53), and a 5.6 GHz band (W56). For this reason, the channel bands do not overlap each other and there is no interference between channels in the 5 GHz band.

Figure 3:
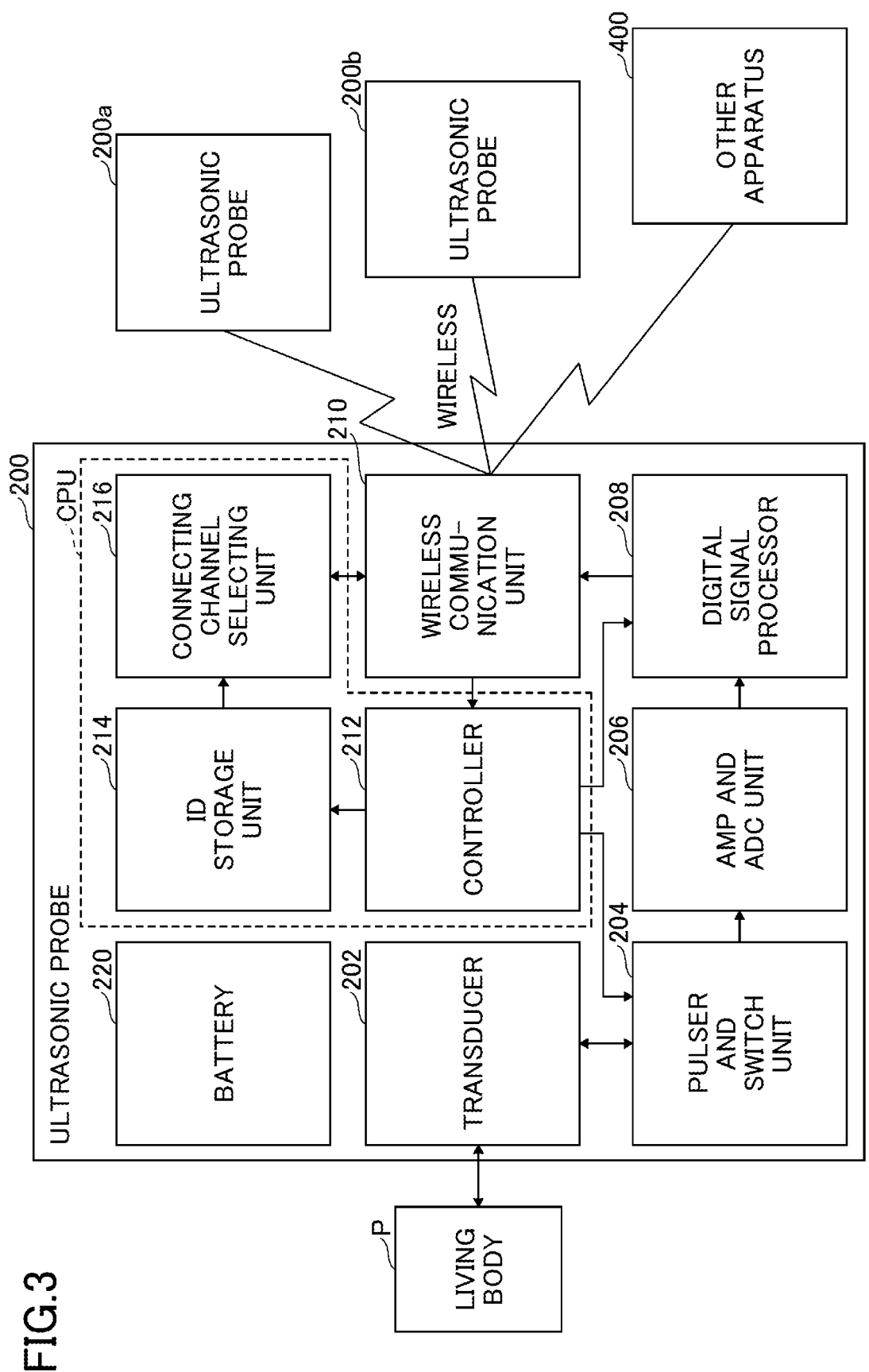
FIG. 3 is a diagram depicting an example of an ultrasonic probe of FIG. 1 detecting an access point to determine a channel to connect.

FIG. 3 depicts an example where the ultrasonic probe 200 of FIG. 1 detects access points to determine a channel to connect. The ultrasonic probe 200 obtains SSID of the access points connected to all Wi-Fi channels when determining a channel to connect. In the example depicted in FIG. 3, apparatuses from which SSID have been obtained include ultrasonic probes 200a and 200b of types the same as or similar to the type of the ultrasonic probes 200 and another apparatus 400 that is different from an ultrasonic probe.

Figure 4:
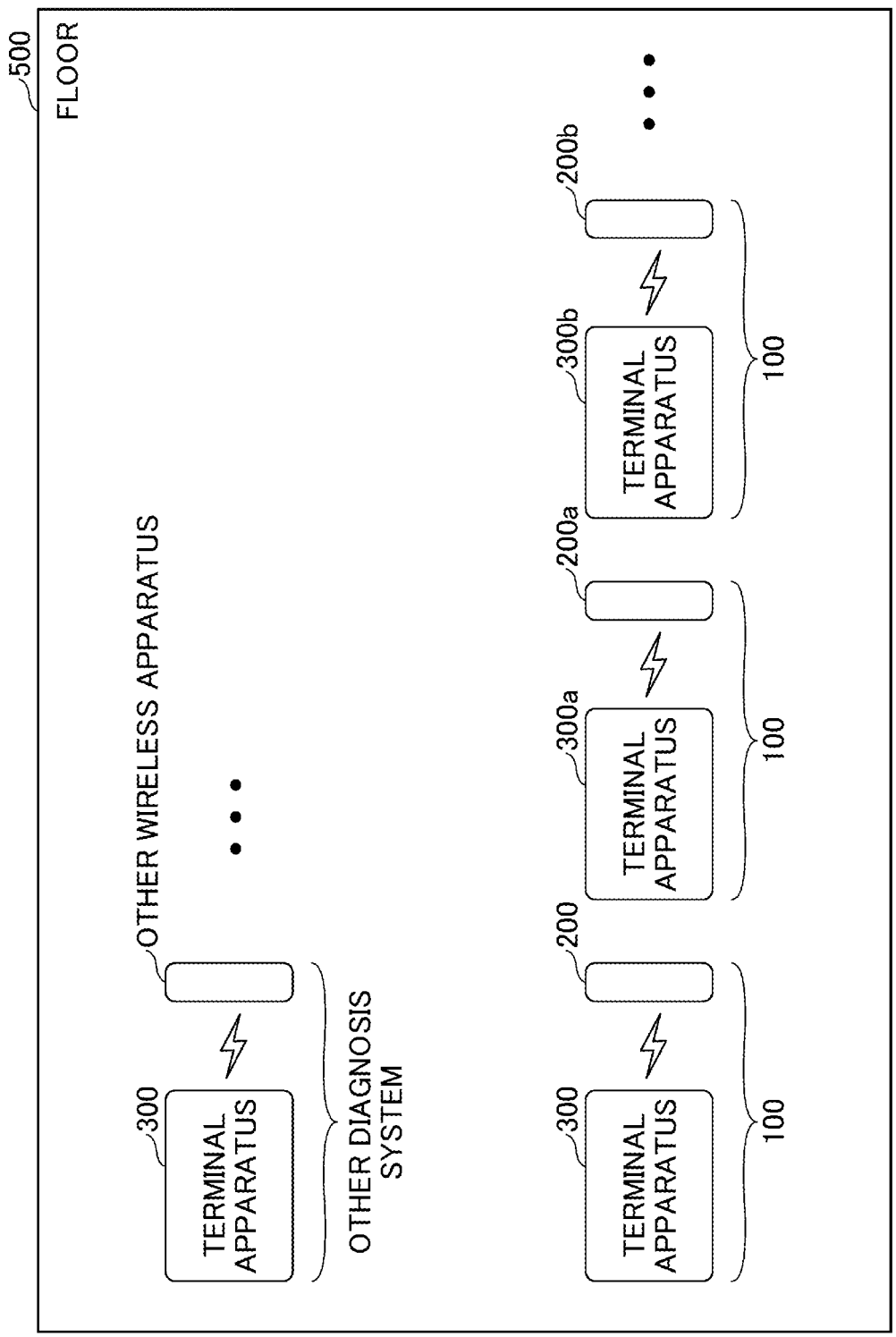
FIG. 4 is a diagram depicting an example of an environment in which the ultrasonic diagnostic system of FIG. 1 is used.

FIG. 4 depicts an example of a use environment of the ultrasonic diagnostic system 100 of FIG. 1. For example, a plurality of ultrasonic diagnostic systems 100 and another diagnostic system may be used on a single floor 500 in a medical institution or a physical examination institution. For example, the another diagnostic system includes a terminal apparatus 300 and another wireless apparatus connected to the terminal apparatus 300.

A Wi-Fi coverage corresponds to the entire area of the floor 500 so that a Wi-Fi radio wave reaches any location. The floor 500 is typically partitioned by partitions or the like, although not depicted. The ultrasonic probe 200 (or 200a or 200b) and terminal apparatus 300 (or 300a or 300b) are wirelessly connected together without a router. The terminal apparatus 300 and the another wireless apparatus of the another diagnostic system are also wirelessly connected without a router.

If a plurality of systems including the ultrasonic diagnostic system 100 are used, the same channel may be used. For example, when the plurality of ultrasonic probes 200, 200a, and 200b of the same type are used on the floor, a probability that the same channel is used by these ultrasonic probes is high. Further, sizes of ultrasonic image data to be transmitted by the ultrasonic probes 200, 200a, and 200b to the terminal apparatuses 300, 300a, and 300b are larger than data sizes of data other than the image data, and therefore, a ratio of a bandwidth used for transmitting the image data with respect to a bandwidth of the connected channel is large accordingly. Thus, if the ultrasonic probe 200b is connected to a channel while the ultrasonic probes 200 and 200a are connected also to the same channel on the floor 500, it may be difficult to continue communication at each of the ultrasonic probe 200, 200a, and 200b.

The ultrasonic probes 200, 200a, and 200b are preferably connected to channels, if possible, different from a channel to which the another wireless apparatus that transmits unknown data size is connected. Therefore, it is desired to connect the ultrasonic probes 200, 200a, and 200b to vacant or non-congested channels. In the following description, the ultrasonic probes 200, 200a, and 200b may be referred to as ultrasonic probes 200 if they are described without being distinguished from each other.

Figure 5:
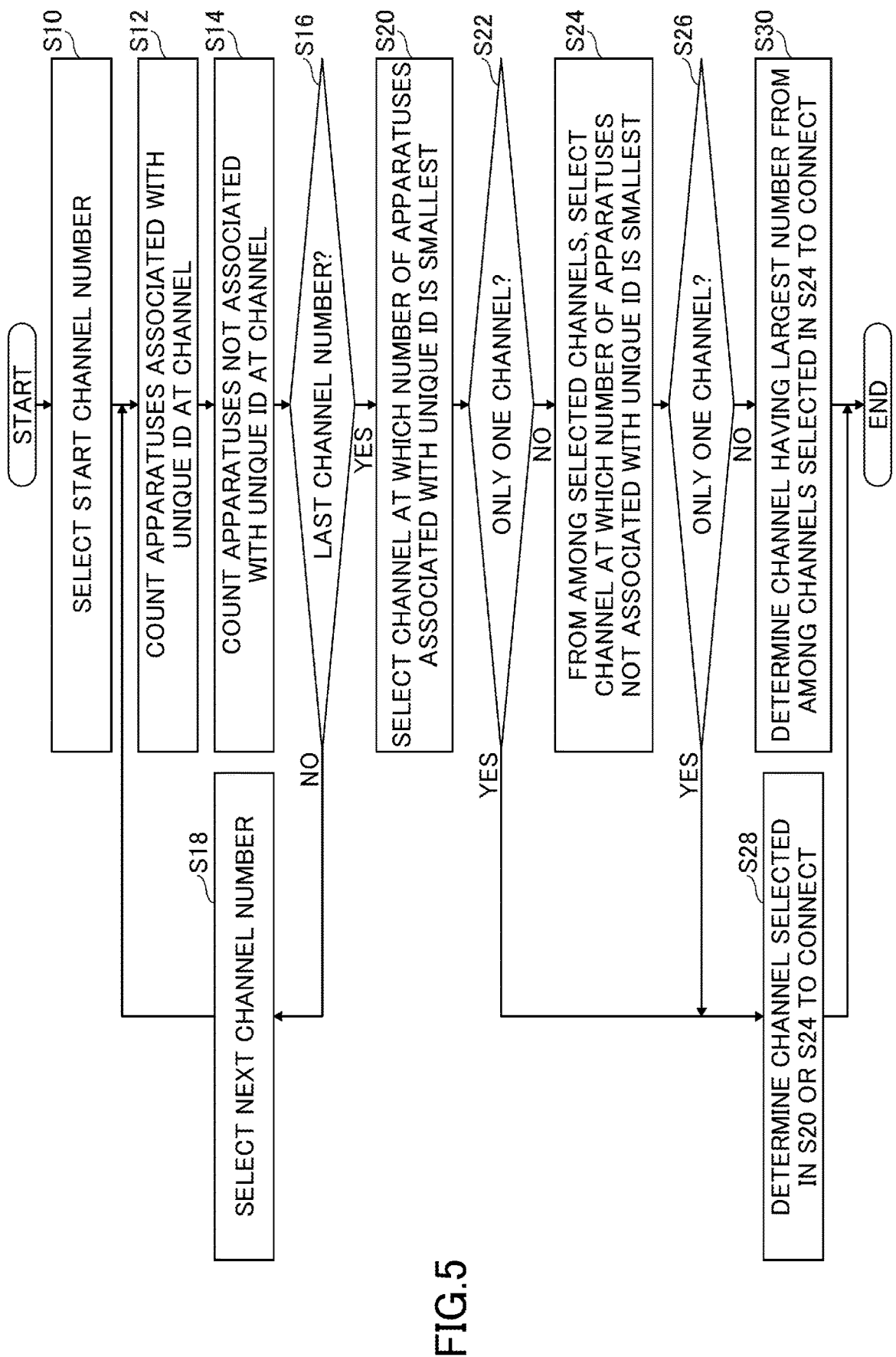
FIG. 5 is a diagram depicting an example of operations of the ultrasonic probe of FIG. 1 to determine a channel to connect.

FIG. 5 depicts an example of operations in which the ultrasonic probe of FIG. 1 determines a channel to connect. For example, the operation flow depicted in FIG. 5 is implemented as a result of a control program being executed by the CPU of the ultrasonic probe 200 to function as the connecting channel selecting unit 216 of FIG. 1. That is, FIG. 5 depicts an example of a method of controlling the ultrasonic probe 200 and an example of the control program for controlling the ultrasonic probe 200. FIG. 5 will be described assuming that the ultrasonic probe 200 uses the Wi-Fi 2.4 GHz band, although also the Wi-Fi 5 GHz band may be used. Alternatively, the operation flow of FIG. 5 may be performed under the condition where a wireless network other than a Wi-Fi network is used.

First, in step S10, the connecting channel selecting unit 216 selects a start channel number. For example, the connecting channel selecting unit 216 selects "1" indicating the channel 1ch depicted in FIG. 2 as a start channel number. Next, in step S12, the connecting channel selecting unit 216 counts other ultrasonic probes 200 connected to the selected channel and associated with the unique ID stored in the ID storage unit 214.

Next, in step S14, the connecting channel selecting unit 216 counts other apparatuses connected to the selected channel and not associated with the unique ID stored in the ID storage unit 214. It is noted that, the connecting channel selecting unit 216 causes the wireless communication unit 210 to transmit a probe request, and determines whether an apparatus is another ultrasonic probe 200 associated with the unique ID or another apparatus not associated with the unique ID based on SSID included in a response to the probe request from the apparatus.

Next, in step S16, the connecting channel selecting unit 216 determines whether the number of the selected channel is the final channel number. The connecting channel selecting unit 216 performs step S20 when the number of the selected channel is the final channel number, and performs step S18 when the number of the selected channel is not the final channel number. In step S18, the connecting channel selecting unit 216 selects the next channel number and returns to step S12. For example, with regard to the Wi-Fi 2.4 GHz band depicted in FIG. 2, a loop of steps S12, S14, S16, and S18 is performed on a channel sequentially from 1ch through 14ch, and the final channel number is "14" indicating 14ch.

In step S20, the connecting channel selecting unit 216 selects a channel, at which the number of the counted other ultrasonic probes 200 associated with the unique ID is smallest, from among the 14 channels. Note that there may be a plurality of channels, at each of which the number of the counted other ultrasonic probes 200 associated with the unique ID is smallest. Next, in step S22, when the number of channels selected in step S20 is 1, the connecting channel selecting unit 216 performs step s28; and, when the number of channels selected in step S20 is 2 or more, the connecting channel selecting unit 216 performs step S24.

In step S24, the connecting channel selecting unit 216 selects a channel, at which the number of the counted other apparatuses not associated with the unique ID is smallest, from among the plurality of channels selected in step S20. In some cases, there may be a plurality of channels, at each of which the number of the counted other apparatuses not associated with the unique ID is smallest. Next, in step S26, when the number of channels selected in step S24 is 1, the connecting channel selecting unit 216 performs step S28; and, when the number of channels selected in step S24 is 2 or more, the connecting channel selecting unit performs step S30.

In step S28, the connecting channel selecting unit 216 determines to connect to the channel selected in step S20 or S24 and ends the process of determining a channel to connect. In step S30, the connecting channel selecting unit 216 determines to connect to a channel having the greatest channel number from among the plurality of channels selected in step S17, and ends the process of determining a channel to connect. For example, the connecting channel selecting unit 216 indicates identification information (i.e., a channel number, etc.) of the channel determined to be connected to the wireless communication unit 210. The wireless communication unit 210 then sets the channel indicated by the connecting channel selecting unit 216, and connects to the set channel based on a connecting instruction from the terminal apparatus 300.

Thus, in the first embodiment, the connecting channel selecting unit 216 connects to a channel having the smallest number of connected ultrasonic probes 200 of similar types. In a case where there are a plurality of channels each having the smallest number of connected ultrasonic probes 200 of similar types, the connecting channel selecting unit 216 connects to a channel having the smallest number of the counted other apparatuses not associated with the unique ID from among the plurality of channels. In a case where there are a plurality of channels, each having the smallest number of the counted other apparatuses not associated with the unique ID, the connecting channel selecting unit 216 connects to a channel having the greatest channel number from among the plurality of channels. In this regard, for example, the ultrasonic probe 200 is connected to a channel having a smaller channel number in many cases.

This allows connection to a channel having the least congested band from among a plurality of channels. Accordingly, by connecting to a channel at which the number of ultrasonic probes 200 of similar types is small, wireless communication between the ultrasonic probe 200 and the terminal apparatus 300 can be performed satisfactorily even when a plurality of ultrasonic diagnostic systems 100 are used in a common space.

Second Embodiment

Figure 6:
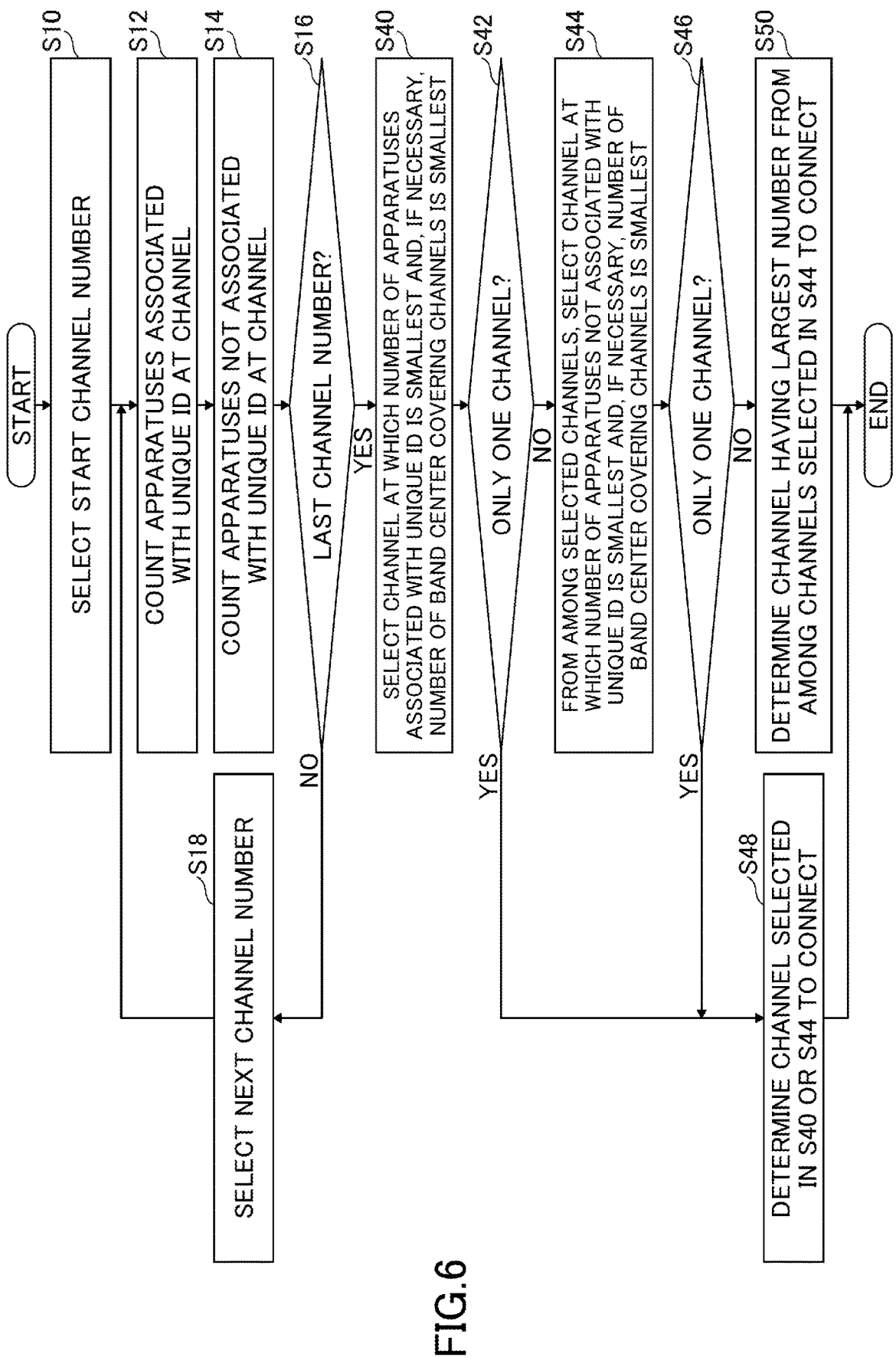
FIG. 6 is a diagram depicting an example of operations of an ultrasonic probe in a second embodiment to determine a channel to connect.

FIG. 6 depicts an example of operations of the ultrasonic probe 200 in a second embodiment to determine a channel to connect. For the same operations as depicted in FIG. 5, the same step numbers are given and the detailed description is omitted. A circuit configuration of the ultrasonic probe 200 in the present embodiment and a system configuration of the ultrasonic diagnostic system 100 including the ultrasonic probe 200 are substantially the same as those of FIG. 1. However, a program that the CPU of the ultrasonic probe 200 executes to determine a channel to connect is different from that of the first embodiment. In other words, a function of the connecting channel selecting unit 216 is different from that of the first embodiment.

An operation flow depicted in FIG. 6 is implemented as a result of a control program being executed by the CPU of the ultrasonic probe 200 to function as the connecting channel selecting unit 216 of FIG. 1. That is, FIG. 6 depicts an example of a method of controlling the ultrasonic probe 200 and an example of the control program for controlling the ultrasonic probe 200. For example, the operating flow depicted in FIG. 6 applies when the ultrasonic probe 200 uses a Wi-Fi 2.4 GHz band. It should be noted that the operating flow depicted in FIG. 6 may be applied also when using another network in which a band of a channel overlaps a band of another channel.

Steps S10, S12, S14, S16, and S18 are the same as those of FIG. 5. That is, for each Wi-Fi channel, the connecting channel selecting unit 216 (FIG. 1) counts connected other ultrasonic probes 200 associated with the unique ID stored in the ID storage unit 214 and counts connected apparatuses not associated with the unique ID stored in the ID storage unit 214.

In step S16, when the currently selected channel is a channel having the final channel number, the connecting channel selecting unit 216 performs step S40 and selects a channel having the smallest number of connected apparatuses associated with the unique ID from among the 14 channels, and if necessary, having the smallest number of "band center covering channels" (described above). That is, if the number of channels, each having the smallest number of connected apparatuses associated with the unique ID is 1, the connecting channel selecting unit 216 does not use the number of band center covering channels for selecting a channel to connect, and selects a channel having the smallest number of connected apparatuses associated with the unique ID from among the 14 channels. If the number of channels, each having the smallest number of connected apparatuses associated with the unique ID is 2 or more, the connecting channel selecting unit 216 selects a channel having the smallest number of "band center covering channels" from among the 2 or more channels.

As described above, a "band center covering channel" with respect to a certain channel is a channel whose band covers a band center of the certain channel. For example, with respect to the Wi-Fi 2.4 GHz band depicted in FIG. 2, a case will be assumed where a plurality of other ultrasonic probes 200 are connected to 1ch, 6ch, and 9ch, respectively. In this case, a band center of each of channels 2ch-5ch, 7ch, 8ch, 10ch, and 11ch is covered by a band of any one of the channels 1ch, 6ch, and 9ch. Therefore, with respect to each of channels 2ch-5ch, 7ch, 8ch, 10ch, and 11ch, any one of the channels 1ch, 6ch, and 9ch is a "band center covering channel". In contrast, a band center of each of channels 12ch, 13ch, and 14ch is not covered by a band of any one of the channels 1ch, 6ch, and 9ch. Therefore, with respect to each of channels 12ch, 13ch, and 14ch, none of the channels 1ch, 6ch, and 9ch is a "band center covering channel". The number of "band center covering channels" with respect to each of the channels 2ch-5ch, 10ch, and 11ch is 1, whereas the number of "band center covering channels" with respect to each of the channels 7ch and 8ch is 2.

In some cases, there are a plurality of channels, at each of which the number of band center covering channels is the smallest. For example, assuming that a plurality of other ultrasonic probes 200 are connected to 1ch, 6ch, and 9ch, respectively, there are a plurality of channels 12ch, 13ch, and 14ch, at each of which the number of band center covering channels is the smallest (i.e., "0").

Next, in step S42, when the number of channels selected in step S40 is 1, the connecting channel selecting unit 216 performs step S48; and when the number of channels selected in step S40 is 2 or more, the connecting channel selecting unit 216 performs step S44.

In step S44, the connecting channel selecting unit 216 selects a channel having the smallest number of connected apparatuses not associated with the unique ID and, if necessary, having the number of band center covering channels is the smallest from among the channels selected in step S40. That is, in step S44, when the number of channels each having the smallest number of connected apparatuses not associated with the unique ID is 1, the connecting channel selecting unit 216 does not use the number of band center covering channels for selecting a channel to connect, and selects a channel having the smallest number of connected apparatuses not associated with the unique ID. When there are a plurality of channels each having the smallest number of connected apparatuses not associated with the unique ID, the connecting channel selecting unit 216 selects a channel having the smallest number of band center covering channels from among the plurality of channels. In some cases, there are a plurality of channels each having the smallest number of connected apparatuses not associated with the unique ID and having the smallest number of band center covering channels. In this case, as will be described later, the connecting channel selecting unit 216 performs step S50.

Next, in step S46, when the number of channels selected in step S44 is 1, the connecting channel selecting unit 216 performs step S48; and when the number of channels selected in step S44 is 2 or more, the connecting channel selecting unit 216 performs step S50.

In step S48, the connecting channel selecting unit 216 determines to connect to the channel selected in step S40 or S44, and ends the process of determining a channel to connect. In step S50, the connecting channel selecting unit 216 determines to connect to a channel having the greatest channel number from among the plurality of channels selected in step S44, and ends the process of determining a channel to connect. Subsequent operations to be performed so that ultimately the wireless communication unit 210 connects to the determined channel are the same as those of the first embodiment.

Thus, also in the second embodiment, similarly to the first embodiment, wireless communication between the ultrasonic probe 200 and the terminal apparatus 300 can be satisfactorily performed by connecting to a channel having the least congested band from among a plurality of channels. Further, in the second embodiment, when bands of channels overlap each other in a wireless network, wireless communication between the ultrasonic probe 200 and the terminal apparatus 300 can be further improved by selecting a channel having a small amount of band overlapping.

Third Embodiment

Figure 7:
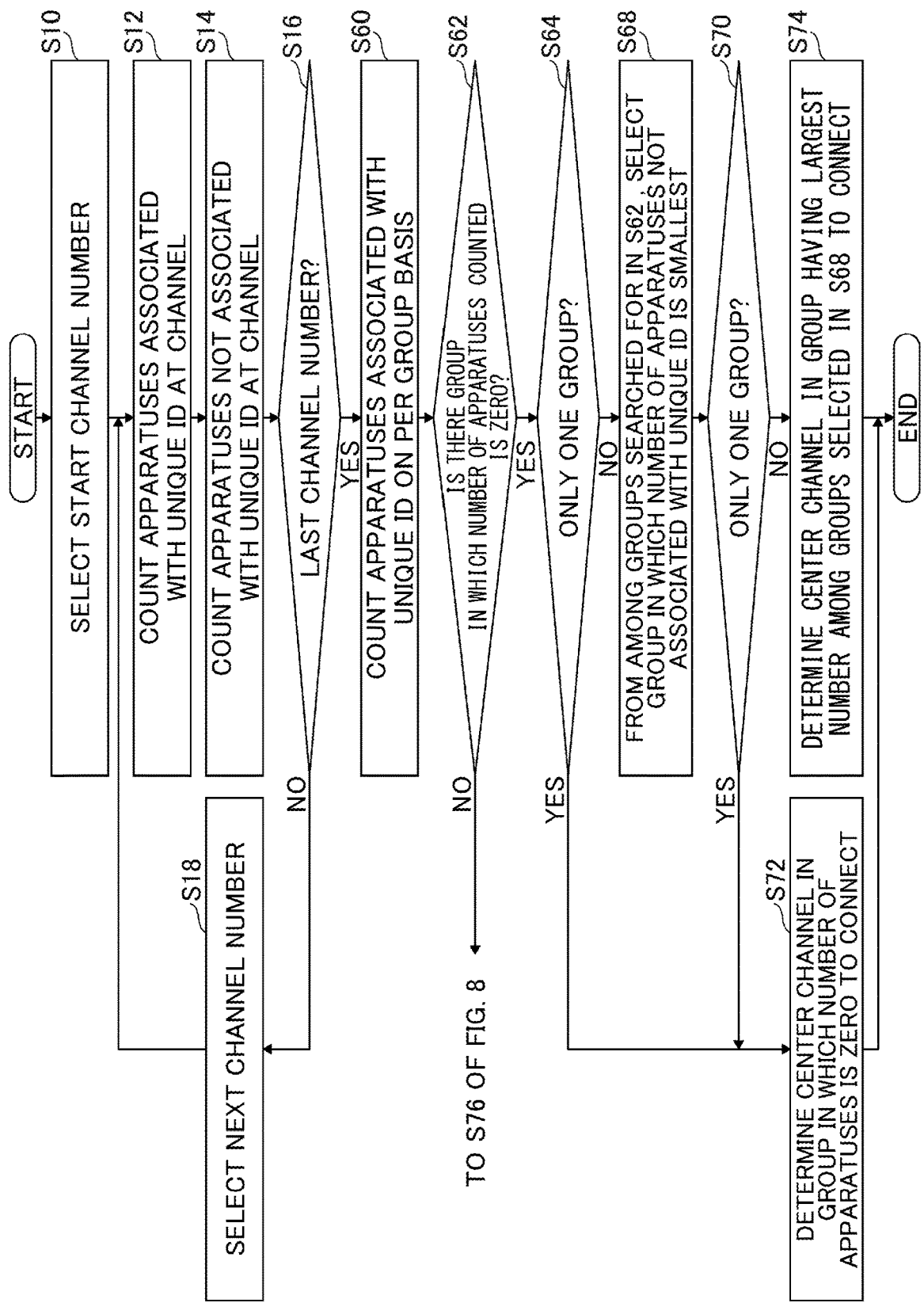
FIGS. 7-8 are diagrams depicting an example of operations of an ultrasonic probe in a third embodiment to determine a channel to connect.
Figure 8:
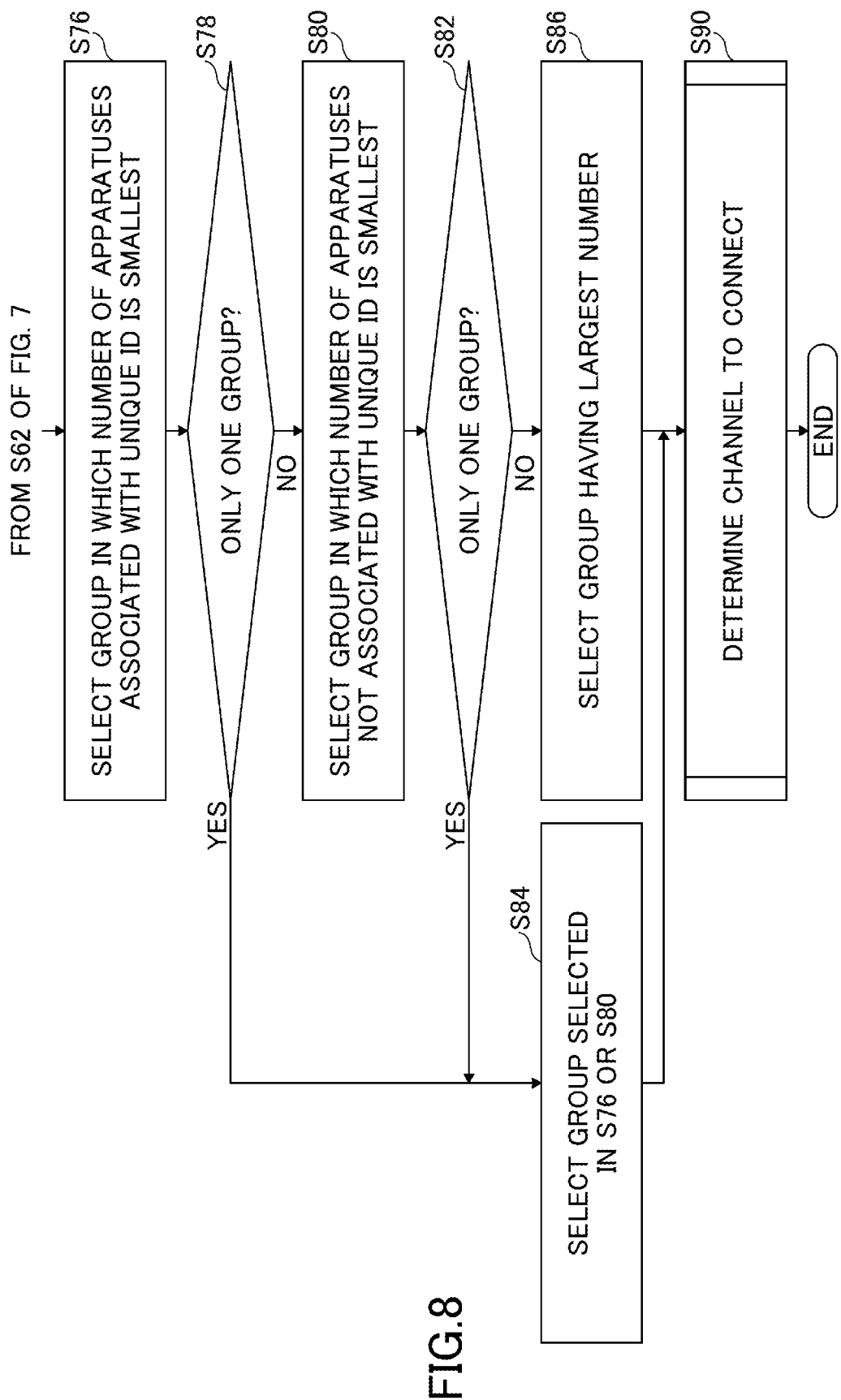

FIGS. 7 and 8 depict an example of operations of the ultrasonic probe in a third embodiment to determine a channel to connect. For the same operations as those depicted in FIG. 5, the same step numbers are given and the detailed description is omitted. A circuit configuration of the ultrasonic probe 200 in the present embodiment and a system configuration of the ultrasonic diagnostic system 100 including the ultrasonic probe 200 are substantially the same as those of FIG. 1. However, a program that the CPU of the ultrasonic probe 200 executes to determine a channel to connect is different from that of the first embodiment. In other words, a function of the connecting channel selecting unit 216 is different from that of the first embodiment.

The operation flow depicted in FIG. 7 is implemented as a result of a control program being executed by the CPU of the ultrasonic probe 200 to function as the connecting channel selecting unit 216 of FIG. 1. That is, FIG. 7 depicts an example of a method of controlling the ultrasonic probe 200 and an example of the control program for controlling the ultrasonic probe 200. FIG. 7 will be described assuming that the ultrasonic probe 200 uses the Wi-Fi 2.4 GHz band, although also the Wi-Fi 5 GHz band may be used instead. Alternatively, the operation flow of FIG. 5 may be performed under the condition where a wireless network other than a Wi-Fi network is used.

In the present embodiment, 14 channels 1ch-14ch in the Wi-Fi 2.4 GHz band are grouped into four groups, with each group having a center channel. For example, a group 1 includes 1ch-3ch and has a center channel 1ch. A group 2 includes 4ch-8ch and has a center channel 6ch. A group 3 includes 9ch-13ch and has a center channel 11ch. A group 4 includes ch14 and has a center channel 14ch. The bands of the four center channels 1ch, 6ch, 11ch, and 14ch do not overlap each other, as depicted by thick lines in FIG. 2, avoiding communication interference with each other.

Steps S10, S12, S14, S16, and S18 are the same as those of FIG. 5. That is, for each Wi-Fi channel, the connecting channel selecting unit 216 (FIG. 1) counts connected other ultrasonic probes 200 associated with the unique ID stored in the ID storage unit 214 and connected apparatuses not associated with the unique ID stored in the ID storage unit 214.

When a number of a selected channel is a final channel number in step S16, the connecting channel selecting unit 216 performs step S60 and counts, on a per group basis, apparatuses associated with the unique ID and connected to the channels belonging to the group. Next, in step S62, when there is a group, in which the number of apparatuses associated with the unique ID counted in step S60 is zero, the connecting channel selecting unit 216 performs step S64, whereas, when there is no group, in which the number of apparatuses associated with the unique ID counted in step S60 is zero, the connecting channel selecting unit 216 performs step S76 of FIG. 8. That is, when all the groups are connected with apparatuses associated with the unique ID, the connecting channel selecting unit 216 performs step S76 of FIG. 8.

In Step S64, when the number of groups, in each of which the number of apparatuses associated with the unique ID counted in step S60 is zero, is 1, the connecting channel selecting unit 216 performs step S72, whereas, when the number of groups, in each of which the number of apparatuses associated with the unique ID counted in step S60 is zero, is 2 or more, the connecting channel selecting unit 216 performs step S68.

In step S68, the connecting channel selecting unit 216 selects a group having the smallest number of connected apparatuses not associated with the unique ID from among the plurality of groups, searched for in step S62, in each of which group the number of apparatuses associated with the unique ID is zero. In some cases, there are a plurality of channels each having the smallest number of connected apparatuses not associated with the unique ID. Next, in step S70, when the number of groups selected in step S68 is 1, the connecting channel selecting unit 216 performs step S72, whereas, when the number of groups selected in step S68 is 2 or more, the connecting channel selecting unit 216 performs step S74.

In step S72, the connecting channel selecting unit 216 determines to connect to a center channel of a group, searched for in step S62 or selected in step S68, in which group the number of connected apparatuses not associated with the unique ID is zero, and ends the process of determining a channel to connect. In step S74, the connecting channel selecting unit 216 determines to connect to a center channel of a group having the greatest group number from among the plurality of groups selected in step S68, and ends the process of determining a channel to connect. Subsequent operations to be performed so that ultimately the wireless communication unit 210 connects to the determined channel are the same as those of the first embodiment.

In step S76 of FIG. 8, the connecting channel selecting unit 216 selects a group having the smallest number of connected apparatuses associated with the unique ID from among the plurality of groups each including a channel to which the number of connected apparatuses associated with the unique ID is 1 or more. In some cases, there are a plurality of groups each having the smallest number of connected apparatuses associated with the unique ID. Next, in step S78, when the number of groups selected in step S76 is 1, the connecting channel selecting unit 216 performs step S84, whereas, when the number of groups selected in step S76 is 2 or more, the connecting channel selecting unit 216 performs step S80.

In step S80, the connecting channel selecting unit 216 selects a group having the smallest number of connected apparatuses not associated with the unique ID from among the plurality of groups selected in step S76. In some cases, there are a plurality of groups each having the smallest number of connected apparatuses not associated with the unique ID. Next, in step S82, when the number of groups selected in step S80 is 1, the connecting channel selecting unit 216 performs step S84, whereas, when the number of groups selected in step S80 is 2 or more, the connecting channel selecting unit 216 performs step S86.

In step S84, the connecting channel selecting unit 216 selects a group selected in step S76 or step S80, and then performs step S90. In step S86, the connecting channel selecting unit 216 selects a group having the greatest group number from among the plurality of groups selected in step S80, and then performs step S90.

In step S90, the connecting channel selecting unit 216 determines a channel to connect, and ends the process. An example of step S90 is depicted in FIG. 9.

Figure 9:
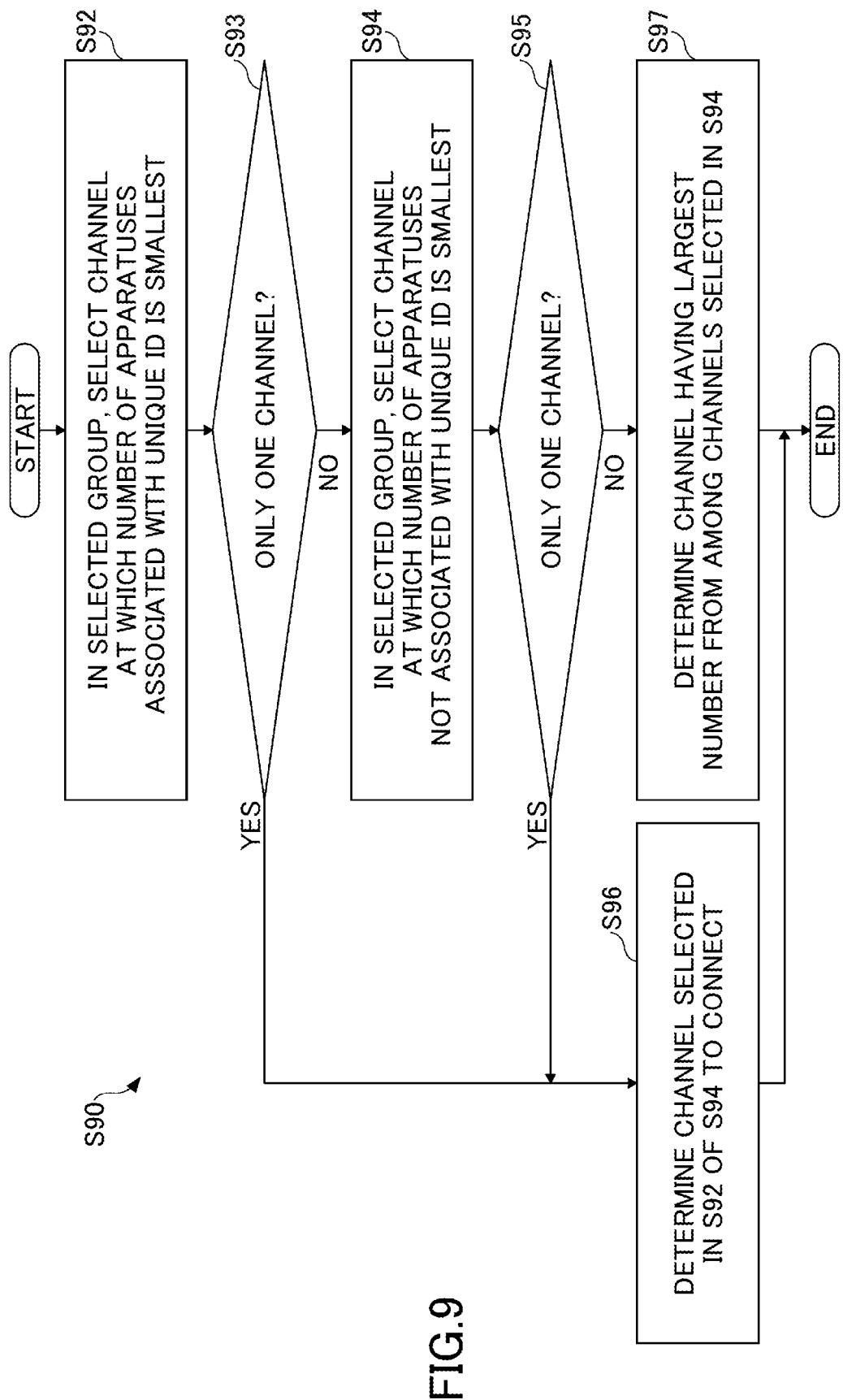
FIG. 9 is a diagram depicting an example of a process of step S90 of FIG. 8.

FIG. 9 depicts an example of step S90 of FIG. 8. First, in step S92, the connecting channel selecting unit 216 selects a channel having the smallest number of connected apparatuses associated with the unique ID from among the channels belonging to the group selected in step S84 or step S86 of FIG. 8. In some cases, there are a plurality of channels, each having the smallest number of connected apparatuses associated with the unique ID. In addition, when the group 4 having only the ch14 is selected in step S84 or S86, ch14 is inevitably selected in step S92.

Next, in step S93, when the number of channels selected in step S92 is 1, the connecting channel selecting unit 216 performs step S96, whereas, when the number of channels selected in step S92 is 2 or more, the connecting channel selecting unit 216 performs step S94.

In step S94, the connecting channel selecting unit 216 selects a channel having the smallest number of connected apparatuses not associated with the unique ID from among the channels belonging to the group selected in step S84 or step S86 of FIG. 8. In some cases, there are a plurality of channels each having the smallest number of connected apparatuses not associated with the unique ID. Next, in step S95, when the number of channels selected in step S94 is 1, the connecting channel selecting unit 216 performs step S96, whereas, when the number of channels selected in step S94 is 2 or more, the connecting channel selecting unit 216 performs step S97.

In step S96, the connecting channel selecting unit 216 determines to connect to the channel selected in step S92 or step S94, and ends the process of determining a channel to connect. In step S97, the connecting channel selecting unit 216 determines to connect to a channel having the greatest channel number from among the plurality of channels selected in step S94, and ends the process of determining a channel to connect. Subsequent operations to be performed so that ultimately the wireless communication unit 210 connects to the determined channel are the same as those of the first embodiment.

As described above, also in the third embodiment, similarly to the first embodiment, wireless communication between the ultrasonic probe 200 and the terminal apparatus 300 can be performed satisfactorily by connecting to a channel having the least congested band from among a plurality of channels. Further, in the third embodiment, wireless communication between the ultrasonic probe 200 and the terminal apparatus 300 can be performed satisfactorily by connecting to a channel included in a group in which apparatuses associated with the unique ID are not connected, from among a plurality of groups each including a predetermined number of channels. In this case, by connecting to a center channel, a band of which does not overlap a band of a center channel of another group, it is possible to prevent bands used by ultrasonic probes from overlapping each other when the ultrasonic probes 200 are connected to channels of a plurality of groups.

Fourth Embodiment

Figure 10:
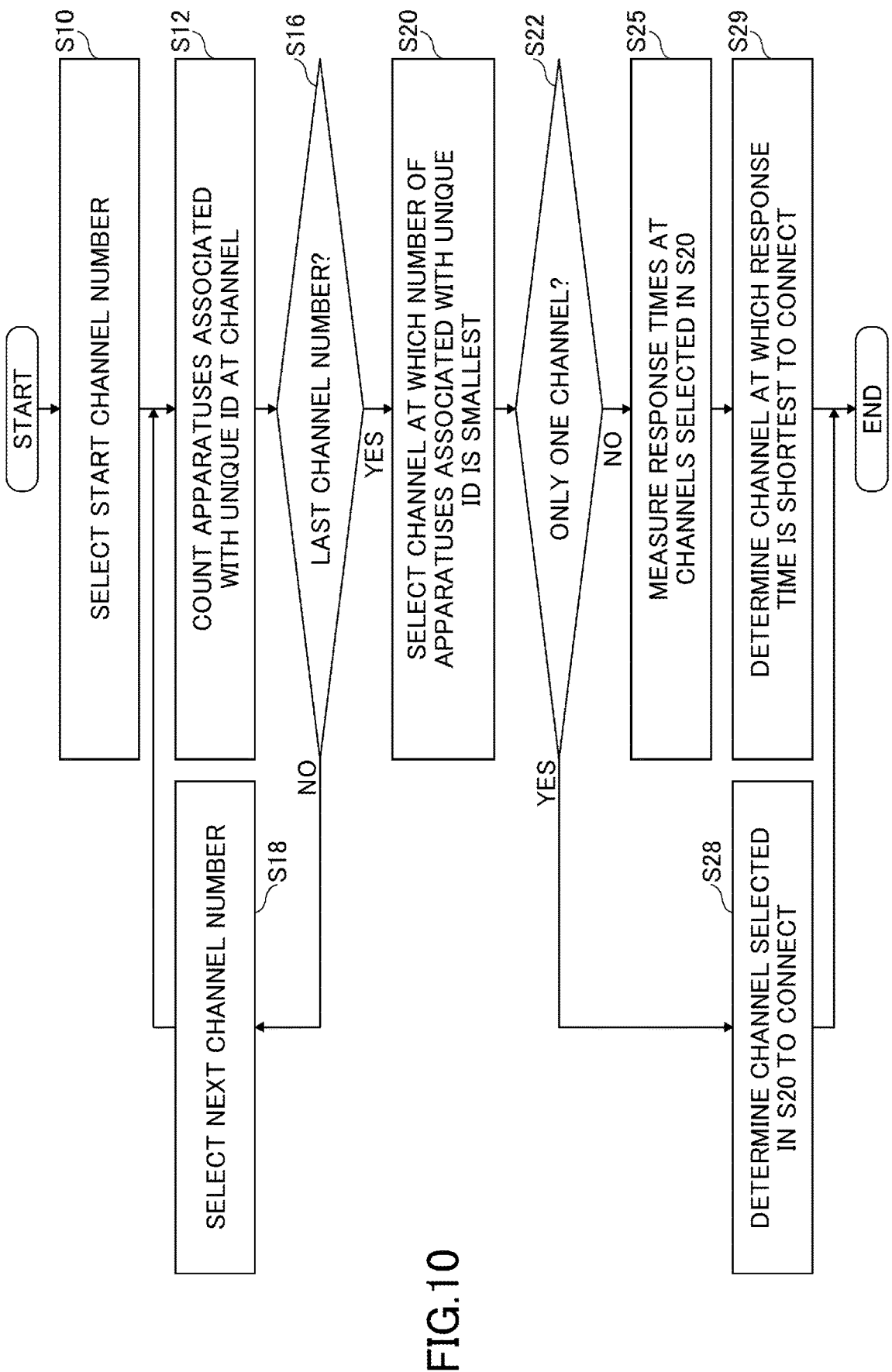
FIG. 10 is a diagram depicting an example of operations of an ultrasonic probe in a fourth embodiment to determine a channel to connect.

FIG. 10 depicts an example of operations of the ultrasonic probe in a fourth embodiment to determine a channel to connect. For the same operations as those depicted in FIG. 5, the same step numbers are given and the detailed description is omitted. A circuit configuration of the ultrasonic probe 200 in the present embodiment and a system configuration of the ultrasonic diagnostic system 100 including the ultrasonic probe 200 are substantially the same as those of FIG. 1. However, a program that the CPU of the ultrasonic probe 200 executes to determine a channel to connect is different from that of the first embodiment. In other words, the function of the connecting channel selecting unit 216 is different from that of the first embodiment.

The operation flow depicted in FIG. 10 is implemented as a result of a control program being executed by the CPU and the corresponding function of the connecting channel selecting unit 216 of FIG. 1 being performed. That is, FIG. 10 depicts an example of a method of controlling the ultrasonic probe 200 and an example of a program of controlling the ultrasonic probe 200. In FIG. 10, the ultrasonic probe 200 is described as using the Wi-Fi 2.4 GHz band, although also the Wi-Fi 5 GHz band of Wi-Fi may be used instead. Alternatively, the operations of FIG. 10 may be applied to a case of using a wireless network other than a Wi-Fi network.

Steps S10, S12, S16, S18, S20, S22, and S28 are the same as those of FIG. 5. In the present embodiment, step S14 in FIG. 5 is not performed. That is, the connecting channel selecting unit 216 (see FIG. 1) counts connected other ultrasonic probes 200 associated with the unique ID stored in the ID storage unit 214 on a per Wi-Fi channel basis. The connecting channel selecting unit 216 selects a channel having the smallest number of connected apparatuses associated with the unique ID and determines to connect to the channel when the number of thus selected channels is 1.

When there are a plurality of channels selected in in step S20, the connecting channel selecting unit 216 performs step S25 and transmits a ping command of a fixed size (for example, 1000 bytes) to any one of apparatuses connected to each of the plurality of channels selected in step S20. The connecting channel selecting unit 216 measures a corresponding response time. Next, in step S29, the connecting channel selecting unit 216 determines to connect to a channel having the shortest response time and ends the process of determining a channel to connect. Subsequent operations to be performed so that ultimately the wireless communication unit 210 connects to the determined channel are the same as those of the first embodiment.

For example, if unknown apparatuses not associated with the unique ID are connected to a channel, a congestion degree of a band of the channel cannot be determined by only the number of the connected apparatuses. In the present embodiment, by measuring a response time of each channel, a degree of band congestion can be determined, and thus, it is possible to improve an accuracy of identifying a less congested channel to connect, as compared to a case where a channel to connect is determined based on the number of connected apparatuses.

Thus, in the fourth embodiment, similarly to the first embodiment, wireless communication between the ultrasonic probe 200 and the terminal apparatus 300 can be performed satisfactorily by connecting to a channel having the least congested band from among a plurality of channels. Furthermore, in the fourth embodiment, when there are a plurality of channels each having the same number of connected apparatuses associated with the unique ID, accuracy of connecting to a less congested channel can be improved by determining a channel to connect in accordance with a response time measured using a ping command. In addition, as a result of measuring response times of apparatuses connected to a plurality of channels selected in step S20, it is possible to shorten a measurement time compared to a case where the response times of the apparatuses connected to all channels are measured. Accordingly, a time required for a process of determining a channel to connect can be reduced.

Fifth Embodiment

Figure 11:
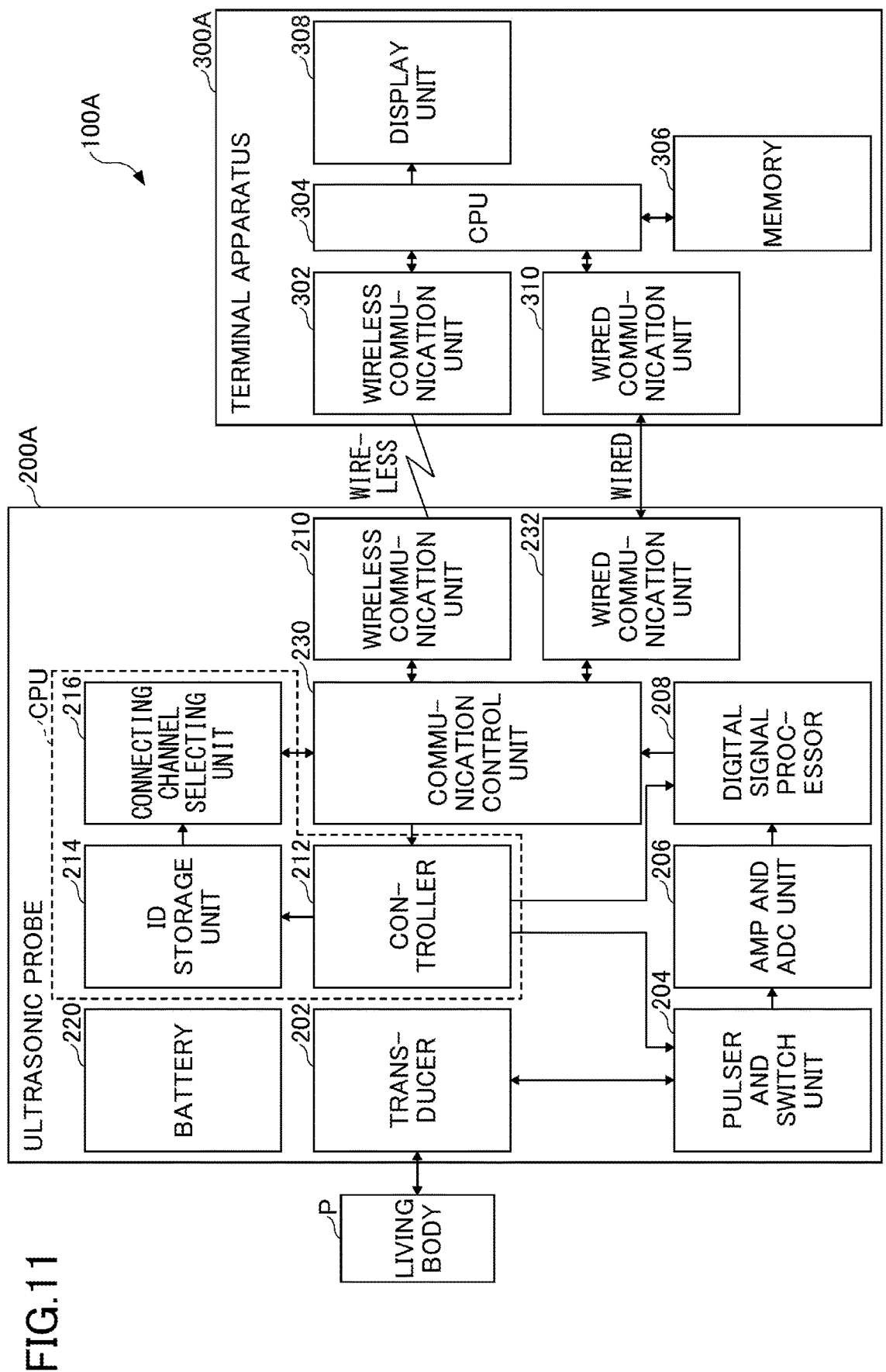
FIG. 11 is a diagram depicting an example of a configuration of an ultrasonic diagnostic system according to a fifth embodiment.

FIG. 11 depicts an example of a configuration of an ultrasonic diagnostic system 100A according to a fifth embodiment. For elements substantially the same as those of FIG. 1, the same numerals are used, and the detailed descriptions are omitted. The ultrasonic diagnostic system 100A depicted in FIG. 11 includes an ultrasonic probe 200A and a terminal apparatus 300A. The ultrasonic probe 200A and the terminal apparatus 300A communicate with each other in a wireless or wired manner. For example, the terminal apparatus 300A may be a general purpose terminal, such as a tablet terminal.

The ultrasonic probe 200A is different from the ultrasonic probe 200 of FIG. 1 in that a communication control unit 230 and a wired communication unit 232 are added. The terminal apparatus 300A is different from the terminal apparatus 300 of FIG. 1 in that a wired communication unit 310 is added. For example, the wired communication units 232 and 310 have universal serial bus (USB) interfaces and are connected to each other via a USB cable.

The communication control unit 230 controls the wireless communication unit 210 when communication with the terminal apparatus 300A is performed in a wireless manner; and controls the wired communication unit 232 when communication with the terminal apparatus 300A is performed in a wired manner. For example, when the communication control unit 230 detects that the ultrasonic probe 200A has been connected to the terminal apparatus 300A through the USB cable, the communication control unit 230 preferentially performs wired communication. Thus, for example, when wireless communication is unstable, the ultrasonic probe 200A can be connected to the terminal apparatus 300A by the USB cable, and thus, the wireless communication can be automatically switched to wired communication. In addition, for example, wired communication can be used for the purpose of displaying ultrasonic image data of the living body P (i.e., the subject), obtained from being measured by the ultrasonic probe 200A, at the terminal apparatus 300A reliably in a real-time manner. The connecting channel selecting unit 216 operates when the communication control unit 230 selects wireless communication, performs any one of processes depicted in FIG. 5, FIG. 6, FIGS. 7-9, and FIG. 10, and determines a channel to connect.

Figure 12:
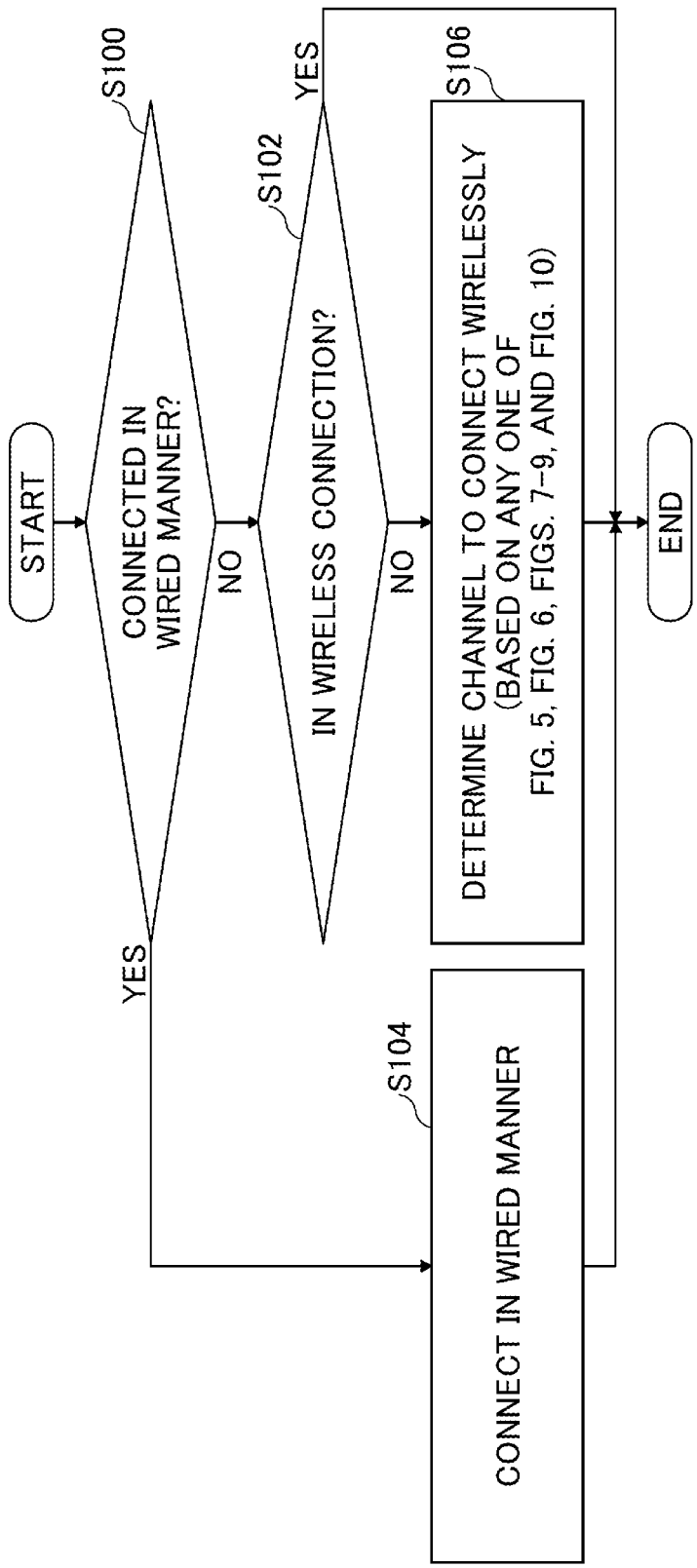
FIG. 12 is a diagram depicting an example of operations of an ultrasonic probe of FIG. 11.

FIG. 12 depicts an example of operations of the ultrasonic probe 200A of FIG. 11. Operations depicted in FIG. 12 are performed at a predetermined frequency.

First, in step S100, the communication control unit 230 determines whether the ultrasonic probe 200A is connected to the terminal apparatus 300A in a wired manner. For example, when the communication control unit 230 is connected to the terminal apparatus 300A through a USB cable, the communication control unit 230 receives from the wired communication unit 232 a detection result that the connection is in a wired manner. When the communication control unit 230 receives the detection result that the connection is in a wired manner from the wired communication unit 232, the communication control unit 230 performs step S104. When the communication control unit 230 does not receive a detection result that the connection is in a wired manner, the communication control unit 230 performs step S102.

In step S102, when the ultrasonic probe 200A is in a wireless connection with the terminal apparatus 300A, the communication control unit 230 ends the process. When the ultrasonic probe 200A is not in a wireless connection with the terminal apparatus 300A, the communication control unit 230 performs step S106. In step S106, the communication control unit 230 causes the connecting channel selecting unit 216 to determine a channel to wirelessly connect and ends the process. The wireless communication unit 210 determines a channel to wirelessly connect through any one of a process of the first embodiment (FIG. 5), a process of the second embodiment (FIG. 6), a process of the third embodiment (FIGS. 7-9), and a process of the fourth embodiment (FIG. 10) based on instructions from the communication control unit 230.

Thus, in the fifth embodiment, similarly to the first embodiment, wireless communication between the ultrasonic probe 200 and the terminal apparatus 300 can be satisfactorily performed by connecting to a channel having the least congested band from among a plurality of channels. Further, in the fifth embodiment, when wireless communication between the ultrasonic probe 200A and the terminal apparatus 300A is not stable, the wireless communication can be switched to wired communication, and thus, ultrasonic image data can be displayed on the terminal apparatus 300A reliably in a real-time manner.

With regard to the embodiments described above, examples of counting the number of other ultrasonic probes 200 associated with the unique ID stored in the ID storage unit 214 have been described. In this regard, the other ultrasonic probes 200 may be of a plurality of types. In this case, ultrasonic probes 200 may be weighted respectively in accordance with their types, and a channel to connect may be determined in consideration of the weighting. For example, weighting of an ultrasonic probe 200 having a large size of ultrasonic image data to be transmitted and weighting of an ultrasonic probe 200 having a small size of ultrasonic image data to be transmitted may differ from one another. Then, when a plurality of channels are selected as connecting channel candidates, a channel with a small band usage (i.e., a small communication amount) may be determined to connect, in accordance with the weighting. For example, the number of other ultrasonic probes 200 is corrected in a manner of multiplications by weighting factors with respect to the ultrasonic probes.

All examples and conditional language recited herein are intended for pedagogical purposes to aid the reader in understanding the invention and the concepts contributed by the inventors to furthering the art, and are to be construed as being without limitation to such specifically recited examples and conditions, nor does the organization of such examples in the specification relate to a depicting of the superiority and inferiority of the invention. Although ultrasonic probes, ultrasonic diagnostic systems, methods of controlling ultrasonic probes, and non-transitory computer-readable recording mediums have been described with reference to the embodiments, it should be understood that the invention is not limited to these embodiments, and the various changes, substitutions, and alterations could be made hereto without departing from the spirit and scope of the invention.

What is claimed is:

1. An ultrasonic probe, comprising:
    a transducer configured to receive ultrasonic waves reflected from an object and output the received ultrasonic waves as signals;
    a wireless transmitter-receiver configured to perform communication through a wireless network having a plurality of channels and obtain identification information of apparatuses connected to the wireless network from the apparatuses, wherein each of the plurality of channels is associated with at least one of the apparatuses;
    a memory configured to store identification information for identifying other ultrasonic probes from among the apparatuses; and a processor configured to count the other ultrasonic probes connected with the wireless network on a per channel basis with respect to the plurality of channels based on the identification information obtained by the wireless transmitter-receiver and the identification information stored in the memory, wherein a band center of each of the plurality of channels is covered by bands of a predetermined number of channels from among the plurality of channels, wherein the processor is configured to count a number of channels at which a number of the other ultrasonic probes counted by the processor is smallest, and upon determining the number of the channels, the processor is configured to:

in a case where there is only one channel at which the number of the other ultrasonic probes counted by the processor is smallest, determine to connect to, and connect to the only one channel, and in a case where there are two or more channels at each of which the number of the other ultrasonic probes counted by the processor is smallest, determine to connect to, and connect to a channel, a band center of which is covered by bands of fewest channels, from among the two or more channels.

2. An ultrasonic diagnostic system, comprising:
the ultrasonic probe claimed in claim 1; and
a terminal apparatus configured to display an ultrasonic image obtained by the ultrasonic probe.

3. The ultrasonic diagnostic system as claimed in claim 2, wherein:
the processor of the ultrasonic probe is further configured to
control switching between wireless communication and wired communication with the terminal apparatus,
select wireless communication with the terminal apparatus when the ultrasonic probe is not connected with the terminal apparatus in a wired manner, and
determine a channel, from among the plurality of channels of the wireless network, to connect with the terminal apparatus, when selecting wireless communication, and connect the channel.

4. An ultrasonic probe, comprising:
a transducer configured to receive ultrasonic waves reflected from an object and output the received ultrasonic waves as signals;
a wireless transmitter-receiver configured to perform communication through a wireless network having a plurality of channels and obtain identification information of apparatuses connected to the wireless network from the apparatuses, wherein each of the plurality of channels is associated with at least one of the apparatuses;
a memory configured to store identification information for identifying other ultrasonic probes from among the apparatuses; and a processor configured to count the other ultrasonic probes connected with the wireless network on a per channel basis with respect to the plurality of channels based on the identification information obtained by the wireless transmitter-receiver and the identification information stored in the memory,
wherein the processor is configured to count a number of channels at which a number of the other ultrasonic probes counted by the processor is smallest, and upon determining the number of the channels, the processor is configured to:

in a case where there is only one channel at which the number of the other ultrasonic probes counted by the processor is smallest, determine to connect to, and connect to the only one channel, and in a case where there are two or more channels at each of which the number of the other ultrasonic probes counted by the processor is smallest, measure a response time at each of the two or more channels at each of which the number of the other ultrasonic probes counted by the processor is smallest, determine to connect to, and connect to a channel at which the response time measured by the processor is shortest.

5. An ultrasonic probe, comprising:
a transducer configured to receive ultrasonic waves reflected from an object and output the received ultrasonic waves as signals;
a wireless transmitter-receiver configured to perform communication through a wireless network having a plurality of channels and obtain identification information of apparatuses connected to the wireless network from the apparatuses;
a memory configured to store identification information for identifying other ultrasonic probes from among the apparatuses; and
a processor configured to count the other ultrasonic probes connected with the wireless network on a per channel basis with respect to the plurality of channels based on the identification information obtained by the wireless transmitter-receiver and the identification information stored in the memory,
wherein the processor is configured to count other apparatuses, other than the other ultrasonic probes, connected with the wireless network on a per channel basis with respect to the plurality of channels based on the identification information obtained by the wireless transmitter-receiver and the identification information stored in the memory, and
wherein the processor is configured to count a number of channels at which a number of the other ultrasonic probes counted by the processor is smallest, and upon determining the number of the channels, the processor is configured to:

in a case where there is only one channel at which the number of the other ultrasonic probes counted by the processor is smallest, determine to connect to, and connect to the only one channel, and in a case where there are two or more channels at each of which the number of the other ultrasonic probes counted by the processor is smallest, determine to connect to, and connect to a channel at which the number of the other apparatuses counted by the processor is smallest from among the two or more channels.

6. The ultrasonic probe as claimed in claim 5,
wherein the processor is further configured to, in a case where there are two or more channels at each of which the number of the other apparatuses counted by the processor is smallest, determine to connect to, and connect to a channel having a largest channel number from among the two or more channels at each of which the number of the other apparatuses counted by the processor is smallest.

7. The ultrasonic probe as claimed in claim 5, wherein:
a band center of each of the plurality of channels is covered by bands of a predetermined number of channels from among the plurality of channels, and the processor is further configured to, in a case where there are two or more channels at each of which the number of the other apparatuses counted by the processor is smallest, determine to connect to, and connect to a channel, a band center of the channel being covered by bands of fewest channels, from among the two or more channels at each of which the number of the other apparatuses counted by the processor is smallest.

8. The ultrasonic probe as claimed in claim 7,
wherein the processor is further configured to, in a case where there are two or more channels in which a band center of each of the plurality of channels is covered by bands of fewest channels, determine to connect to, and connect to a channel having a largest channel number from among the two or more channels in which the band center of each of the two or more channels is covered by the bands of the fewest channels.

* * * * *